United States Patent [19]

Stoughton

[11] 4,132,781
[45] Jan. 2, 1979

[54] METHOD FOR TREATMENT OF ACNE
[75] Inventor: Richard B. Stoughton, Rancho Santa Fe, Calif.
[73] Assignee: Nelson Research & Development Company, Irvine, Calif.
[21] Appl. No.: 534,229
[22] Filed: Dec. 19, 1974
[51] Int. Cl.² ............................................. A61K 31/71
[52] U.S. Cl. .................................... 424/181; 424/274
[58] Field of Search ................................ 424/181, 274

[56] References Cited
U.S. PATENT DOCUMENTS
3,472,931  10/1969  Stoughton .......................... 424/181

OTHER PUBLICATIONS
Laden, Chemical Abstracts, 73:102083d, (1970).
Merck Index, 8th Edition, (1968), pp. 419-420.
Bobroff, Acne and Related Disorders of Complexion and Scalp, published by Charles, C. Thomas, Springfield, Ill., (1965), pp. 59-61.
Fulton et al., Arch Dermatol., vol. 110, Jul., 1974, pp. 83-86.

*Primary Examiner*—Leonard Schenkman
*Attorney, Agent, or Firm*—Martin A. Voet

[57] ABSTRACT

There is disclosed a topical antibacterial composition and method for topical antibiotic treatment. The method involves contacting the skin of a human or animal with an effective amount of a composition containing an antibiotic of the erythromycin family and 2-pyrrolidone or an N-lower alkyl-2-pyrrolidone. The preferred use of the foregoing composition and method is in the treatment of acne.

2 Claims, No Drawings

METHOD FOR TREATMENT OF ACNE

BACKGROUND OF THE INVENTION

1. Field of the Invention

The invention relates generally to topical antibacterial compositions and a method for topically administering antibiotics. More particularly, the invention relates to compositions and a method for topically administering antibiotics of the erythromycin family.

2. Background of the Prior Art

Vehicles such as USP cold cream, ethanol, isopropanol and various creams, ointments, oils, solvents, and emulsions have been used to apply various active ingredients topically. However, these conventional vehicles are not adequate to provide therapeutically effective amounts of antibacterial agents to be retained in the epidermis or to penetrate into the deeper layers of the skin.

Acne is the name commonly applied to any inflammatory disease of the sebaceous glands; also *acne vulgaris*. The microorganism typically responsible for the acne infections is *Corynebacterium acnes*. Various therapeutic methods for treating acne have been attempted including topical antibacterials, e.g. hexachlorophene, and systemic antibiotics such as tetracycline. While the systemic antibiotic treatments are known to be effective, the topical treatments are not effective.

It has long been known that systemic treatment of acne is not preferred because of side effects resulting from saturation of the entire body with antibiotics and the fact that only the affected skin need be treated. However, despite a long-felt need for a topical treatment for acne, antibiotics generally have been used only systemically to treat acne because there was not heretofore known an antibacterial formulation which could be used topically which would be effective therapeutically in the treatment of acne.

SUMMARY OF THE INVENTION

It has now unexpectedly been discovered that certain active antibiotics may be effectively administered topically through the use of the compositions herein described.

The invention generally relates to a method for treating cutaneous diseases associated with microorganisms by topically administering to humans or animals antibiotics of the erythromycin family whereby therapeutically effective amounts of the antibiotic penetrate into the epidermis and the deeper layers of the skin. The foregoing method is carried out by topically administering to a human or animal an effective amount of a composition containing about 0.1 to about 10% by weight of an antibiotic of the erythromycin family together with about 5 to about 99.9 percent by weight of 2-pyrrolidone or an N-lower alkyl-2-pyrrolidone.

In its preferred embodiment, the invention described herein may be used to temporarily alleviate the signs and symptoms of acne.

DETAILED DESCRIPTION OF THE INVENTION

The term "antibiotic of the erythromycin family" is used herein to refer to a class of antibiotic substances originally elaborated by a strain of *Streptomyces erythreus*.

Typical examples of antibiotics of the erythromycin family include erythromycin, erythromycin ethyl carbonate, erythromycin stearate, erythromycin estolate, erythromycin glucepate, erythromycin propionate, erythromycin ethylsuccinate and erythromycin lactobionate. These compounds and their method of synthesis are shown in U.S. Pat. Nos. 2,823,203, 3,000,874, 2,852,429, 2,761,859, 2,993,833 and 2,862,921.

The amount of antibiotic of the erythromycin family which may be used in the present invention ranges from about 0.1 to about 10 percent by weight and preferably about 1 to about 5 percent by weight of the composition.

2-Pyrrolidone and N-lower alkyl-2-pyrrolidones are available commercially and are made by a number of methods known to those of skill in the art as exemplified by U.S. Pat. Nos. 2,555,353 and 2,267,757. N-lower alkyl-2-pyrrolidones include the straight and branch chain lower alkyl groups having 1-4 carbon atoms. N-methyl-2-pyrrolidone is preferred.

The amount of 2-pyrrolidone or N-lower alkyl-2-pyrrolidone which may be used in the present invention ranges from about 5 to about 99.9 percent and preferably 10-50 percent by weight of the composition.

The composition may be used topically to temporarily alleviate the signs and symptoms of cutaneous infections caused by organisms against which the erythromycin family of antibiotics are effective. The compositions of this invention therefore may be used in the topical treatment of skin conditions associated with microorganisms including impetigo, acne, pyodermias and secondarily infected eczema.

An effective amount of the composition, as the term is used herein, refers to that amount of composition which is effective therapeutically in the desired treatment. The composition is generally applied about 1-4 times daily in conventional amounts, that is, amounts sufficient to thinly spread over the affected areas. The treatment is continued until or sometime after all of the manifestations of the condition being treated have disappeared.

The antibiotics of the erythromycin family described herein may be dissolved in a vehicle of this invention and topically applied to affected areas of the skin in any convenient form, e.g. cream, lotion, spray, solution, etc.

Ingredients which may be used in these formulations include conventional formulating ingredients, such as, for example, Freons, ethyl alcohol, isopropyl alcohol, acetone, polyvinyl pyrrolidone, propylene glycol, fragrances, gel-producing materials, mineral oil, water, stearyl alcohol, stearic acid, spermaceti, sorbitan monooleate, Polysorbate 80, Tween 60, sorbital solutions, methylcellulose, etc.

The antibiotic compositon so applied is carried into and through the epidermis and deeper layers of the skin as well as into follicles and comedones (sebum-plugged follicles which contain C. acnes) in therapeutically effective amounts and thereby successfully may be used to temporarily eliminate the signs and symptons of acne.

Following are specific examples which demonstrate the effectiveness of various forms of this invention.

EXAMPLE I

A clinical and microbiological study was carried out to show the effectiveness of the composition of the present invention in the treatment of acne. 5-6 human subjects with *acne vulgaris* were used in each determination. Formulations A, B and C (Table 1) were applied to each patient's face twice daily in an amount of about 0.5 cc per day. Comedones were removed with an extractor and put into a gelatin capsule. The capsule was dissolved in warm phosphate buffer and an aliquot plated on a special medium in dilutions which were cultured anaerobically for 7 days. The counts of *C. acnes* are expressed as the number of *C. acnes* per milligram of comedone material. Clinical appraisal was carried out at biweekly intervals. The results of the study are shown in Tables 2 and 3 below.

Table 1

| Ingredients | A | B | C |
|---|---|---|---|
| Tetracycline HCl | 1% | — | — |
| Erythromycin | — | 1% | — |
| N-methyl-2-pyrrolidine | 99% | 99% | 100% |

Table 2
Antibacterial Evaluation of Antibiotics Active Against *C. acnes* in the Treatment of Acne

| | Comedone Bacterial (*C. acnes*) Count, #/mg Evaluation time, weeks | | | | |
|---|---|---|---|---|---|
| Preparation | 0 | 2 | 4 | 6 | 8 |
| A | $3 \times 10^7$ | $1 \times 10^7$ | $3 \times 10^6$ | $6 \times 10^6$ | $3 \times 10^7$ |
| B | $4 \times 10^6$ | $4 \times 10^6$ | $1 \times 10^6$ | $3 \times 10^5$ | $2 \times 10^5$ |
| C | $2 \times 10^6$ | $3 \times 10^6$ | $7 \times 10^5$ | $2 \times 10^6$ | $3 \times 10^7$ |

Table 3
Clinical Evaluation in the Treatment of Acne[a]

| | Evaluation time, weeks | | | | |
|---|---|---|---|---|---|
| Preparation | 0 | 2 | 4 | 6 | 8 |
| A | — | 0.7 | 1.0 | 0.8 | 1.1 |
| B | — | 1.5 | 1.8 | 2.1 | 2.2 |
| C | — | 0.5 | 0.6 | 0.7 | 0.9 |

[a]Appraisal based upon following scale:
0 = no response
1 = slight improvement
2 = good improvement
3 = very good improvement
4 = dramatic improvement The results of the foregoing tests show that tetracycline, a commonly used antibiotic in the systemic treatment of acne (Preparation A) is essentially ineffective as is the vehicle alone (Preparation C). However, the results of the foregoing tests shown a good improvement with an erythromycin (formulation B).

EXAMPLE II

The studies of Example I are repeated using erythromycin ethyl carbonate, erythromycin stearate, erythromycin estolate, erythromycin glucepate, erythromycin propionate, erythromycin ethyl succinate and erythromycin lactobionate in the place of erythromycin. Comparable results are obtained.

EXAMPLE III

Example II is repeated, except that the N-methyl-2-pyrrolidone is replaced by each of 2-pyrrolidone, N-ethyl-2-pyrrolidone, N-propyl-2-pyrrolidone and N-isobutyl-2-pyrrolidone. Comparable results are obtained.

EXAMPLE IV.

The following cream formulations are prepared:

| | A | B | C | D |
|---|---|---|---|---|
| Erythromycin | 1% | 1% | 1% | 1% |
| N-methyl-2-pyrrolidone | 25% | 20% | 34% | 42% |
| Stearyl alcohol | 12% | — | — | 10% |
| Stearic acid | — | 19% | 18% | 6% |
| Synthetic spermaceti | 7.5% | — | 2% | 4% |
| Sorbitan monooleate | 1.0% | — | — | — |
| Polysorbate 80 | 5.5% | — | — | — |
| Tween 60 | — | 3.5% | 3.5% | 3.5% |
| Arlacel 60 | — | 3.5% | 3.5% | 1.5% |
| Sorbitol solution | 5.5% | 19.4% | 14% | 10.5% |
| Mineral Oil | — | 2% | — | — |
| Methocel 90 HG-100 | — | 0.2% | 0.2% | 0.2% |
| Fragrances | 0.2% | — | — | — |
| Sodium citrate | 0.5% | — | — | — |
| Water q.s.ad | 100% | 100% | 100% | 100% |

EXAMPLE V

The following solution formulations are prepared:

| | Solutions | | | |
|---|---|---|---|---|
| | A | B | C | D |
| Erythromycin | 1% | 1% | 1% | 1% |
| N-methyl-2-pyrrolidone | 10% | 46.6% | 90% | 33% |
| Isopropyl myristate | 5% | 5% | 5% | — |
| Propylene glycol | — | — | — | 33% |
| Fragrance | 0.1% | 0.1% | 0.1% | 0.1% |
| Adjuvant solvent q.s. ad | ethanol | isopropyl alcohol | acetone | isopropyl alcohol |

EXAMPLE VI

An aerosol form of formulation B of EXAMPLE V is prepared by preparing the following mixture:

| formulation B | 25% |
|---|---|
| Freon[1] | 75% |

[1]Freon is 75/25 Freon 114/12.

EXAMPLE VII

The following gel formulations are prepared:

| | Gel | |
|---|---|---|
| | A | B |
| Erythromycin | 1% | 1% |
| N-methyl-2-pyrrolidone | 96% | 20% |
| Carbopol 934 | 1% | — |
| Carbopol 940 | — | 0.75% |
| Ethanol | — | 50% |
| Ethoxyl 16R | — | 2% |
| Diethanolamine | — | 0.5% |
| di-(2(ethylhexyl)amine | 2% | — |
| water q.s. ad | | |

I claim:

1. A method for temporarily alleviating the signs and symptoms of acne comprising topically administering to human skin an effective amount of a composition comprising about 0.1 to about 10 percent by weight of an antibiotic of the erythromycin family together with about 5 to about 99.9 percent by weight of a compound selected from the group consisting of 2-pyrrolidone and an N-lower alkyl-2-pyrrolidone.

2. A method for temporarily alleviating the signs and symptoms of acne comprising topically administering to humans an effective amount of a composition comprising about 1 to about 5 percent by weight of an erythromycin together with about 10 to about 50 percent by weight N-methyl-2-pyrrolidone.

* * * * *